US011896853B2

(12) United States Patent
Khokhlova et al.

(10) Patent No.: US 11,896,853 B2
(45) Date of Patent: Feb. 13, 2024

(54) TRANSRECTAL ULTRASOUND PROBE FOR BOILING HISTOTRIPSY ABLATION OF PROSTATE, AND ASSOCIATED SYSTEMS AND METHODS

(71) Applicant: University of Washington, Seattle, WA (US)

(72) Inventors: Vera Khokhlova, Seattle, WA (US); Pavel Rosnitskiy, Seattle, WA (US); Petr V. Yuldashev, Moscow (RU); Tatiana D. Khokhlova, Seattle, WA (US); Oleg A. Sapozhnikov, Seattle, WA (US); George R. Schade, Seattle, WA (US)

(73) Assignee: University of Washington, Seattle, WA (US)

( * ) Notice: Subject to any disclaimer, the term of this patent is extended or adjusted under 35 U.S.C. 154(b) by 23 days.

(21) Appl. No.: 16/871,980

(22) Filed: May 11, 2020

(65) Prior Publication Data

US 2020/0353293 A1 Nov. 12, 2020

Related U.S. Application Data

(60) Provisional application No. 62/846,267, filed on May 10, 2019.

(51) Int. Cl.
*A61N 7/02* (2006.01)
*A61B 8/12* (2006.01)
(Continued)

(52) U.S. Cl.
CPC ............... *A61N 7/022* (2013.01); *A61B 8/12* (2013.01); *A61B 8/445* (2013.01);
(Continued)

(58) Field of Classification Search
CPC ............ A61N 7/022; A61N 2007/0039; A61N 2007/0052; A61N 2007/0078; A61B 8/12;
(Continued)

(56) References Cited

U.S. PATENT DOCUMENTS 4,526,168 A * 7/1985 Hassler ............... A61B 8/0833
601/4
8,876,740 B2 11/2014 Canney et al.
(Continued)

FOREIGN PATENT DOCUMENTS

CN 106267593 A 1/2017
EP 3108934 A1 12/2016
(Continued)

OTHER PUBLICATIONS

Tan, Joseph S., et al. "Ultrasound phased arrays for prostate treatment." The Journal of the Acoustical Society of America 109.6 (2001): 3055-3064. (Year: 2001).*

(Continued)

*Primary Examiner* — Amelie R Davis
(74) *Attorney, Agent, or Firm* — Christensen O'Connor Johnson Kindness PLLC

(57) ABSTRACT

Transrectal ultrasound probe for boiling histotripsy ablation of prostate are presented herein. In one embodiment, a method for a transrectal ultrasound treatment uses high intensity focused ultrasound (HIFU). The method includes: generating a boiling histotripsy (BH) therapy ultrasound by a therapy transducer in a frequency range of 1 MHz to 2.8 MHz and a surface intensity range of 10 W/cm2 to 80 W/cm2. The therapy transducer may be about 50 mm long and about 35 mm wide. The method also includes applying the therapy ultrasound by directing ultrasound pulses having ultrasound shock waves to a target tissue at a focal depth of 2.5 cm to 5.5 cm; generating at least one μm-scale vapor
(Continued)

bubble at a target region; growing the at least one vapor bubble to at least one mm-scale bubble; and mechanically disintegrating a surrounding tissue by interactions between mm-scale bubbles and the ultrasound shock waves within a pulse.

20 Claims, 11 Drawing Sheets

(51) Int. Cl.
    *A61B 8/00* (2006.01)
    *A61B 17/32* (2006.01)
    *A61B 17/00* (2006.01)
    *A61N 7/00* (2006.01)

(52) U.S. Cl.
    CPC ............... *A61B 2017/00274* (2013.01); *A61B 2017/320069* (2017.08); *A61N 2007/0039* (2013.01); *A61N 2007/0052* (2013.01); *A61N 2007/0078* (2013.01)

(58) Field of Classification Search
    CPC .......... A61B 8/445; A61B 2017/00274; A61B 2017/320069; A61B 8/085; A61B 2090/3784
    See application file for complete search history.

(56) References Cited

U.S. PATENT DOCUMENTS

| | | | |
|---|---|---|---|
| 9,901,753 B2 | 2/2018 | Cain | |
| 2003/0018255 A1* | 1/2003 | Martin | A61B 17/2251 600/437 |
| 2006/0052706 A1* | 3/2006 | Hynynen | A61N 7/022 600/459 |
| 2006/0241527 A1* | 10/2006 | Muratore | A61N 7/02 601/2 |
| 2007/0041961 A1* | 2/2007 | Hwang | A61K 38/363 424/94.64 |
| 2010/0160781 A1* | 6/2010 | Carter | A61B 8/06 600/439 |
| 2015/0375015 A1 | 12/2015 | Cain | |
| 2017/0000376 A1 | 1/2017 | Partanen | |
| 2017/0072227 A1 | 3/2017 | Khokhlova | |
| 2017/0072228 A1* | 3/2017 | Wang | A61N 7/02 |

FOREIGN PATENT DOCUMENTS

| | | |
|---|---|---|
| KR | 20180074235 A | 7/2018 |
| WO | 2013/103975 A8 | 7/2013 |
| WO | 2017/190159 A1 | 11/2017 |

OTHER PUBLICATIONS

Curiel, Laura, et al. "1.5-D high intensity focused ultrasound array for non-invasive prostate cancer surgery." IEEE transactions on ultrasonics, ferroelectrics, and frequency control 49.2 (2002): 231-242. (Year: 2002).*

Chaussy, Christian G., and Stefan Thüroff. "Transrectal high-intensity focused ultrasound for local treatment of prostate cancer: current role." Journal of Cancer Therapy 4 (2013): 59-73. (Year: 2013).*

Velez-Duran, Marcos. "EDAP Ablatherm® Integrated Imaging High Intensity Focused Ultrasound (HIFU) Indicated for the Treatment of Low Risk, Localized Prostate Cancer." EDAP Technomed, Inc. (2014). (Year: 2014).*

Kreider et al. Rectified growth of histotripsy bubbles. Proc Meet Acoust. 2013: 19(1)). (Year: 2013).*

Khokhlova, V.A., et al., "Initial Assessment of Boiling Histotripsy for Mechanical Ablation of Ex Vivo Human Prostate Tissue," Proceedings of the 6th International Symposium on Focused Ultrasound, Reston, VA, Oct. 21-25, 2018, 7 pages.

Khokhlova, V., et al., "Design of a Transrectal Probe for Boiling Histotripsy Ablation of Prostate," Proceedings of the the 18th International Symposium on Therapeutic Ultrasound, International Society for Therapeutic Ultrasound, Nashville, TN, May 14-17, 2018, 4 pages.

Schade, G.R., et al., "Mechanical Ablation of Human Ex Vivo Prostate Tissue Using Boiling Histotripsy," Proceedings of the Engineering and Urology Society 33rd Annual Meeting, San Francisco, CA, May 18, 2018, 2 pages.

Schade, G.R., et al., "A Preclinical Transrectal Boiling Histotripsy System for Prostate Ablation," Proceedings of the Engineering and Urology Society 34th Annual Meeting, Chicago, IL, May 5, 2019, 1 page.

Canney, M., "Tissue Erosion Using Shock Wave Heating and Millisecond Boiling in HIFU Fields," AIP Conference Proceedings, vol. 1215, pp. 36-39, published online on Mar. 5, 2021.

Daoudi, K.,"In vivo photoacoustics and high frequency ultrasound imaging of mechanical high intensity focused ultrasound (HIFU) ablation," Biomedical Optics Express, Mar. 2017, <https://doi.org/10.1364/BOE.8.002235> [retrieved Feb. 10, 2021], 10 pages.

Eranki, A., "Boiling histotripsy lesion characterization on a clinical magnetic resonance imaging-guided high intensity focused ultrasound system," PLoS One, Mar. 2017, 12(3): e0173867.

Eranki, A., "Mechanical fractionation of tissues using microsecond-long HIFU pulses on a clinical MR-HIFU system," International Journal of Hyperthermia, Feb. 2018 <https://doi.org/10.1080/02656736.2018.1438672> [retrieved Feb. 10, 2021], 13 pages.

Hoogenboom, M., "In vivo MR guided boiling histotripsy in a mouse tumor model evaluated by MRI and histopathology," NMR in Biomedicine, Apr. 2016 <https://doi.org/10.1002/nbm.3520/> [retrieved Feb. 10, 2021], 11 pages.

Khokhlova, T., "Dependence of boiling histotripsy treatment efficiency on HIFU frequency and focal pressure levels," Elsevier, Apr. 2017 <https://dx.doi.org/10.1016/j.ultrasmedbio.2017.04.030> [retrieved Feb. 10, 2021], 11 pages.

Khokhlova, T., "Ultrasound-guided tissue fractionation by high intensity focused ultrasound in an in vivo porcine liver model," PNAS Early Edition, Apr. 2014 <https://pnas.org/cgi/doi/10.1073/pnas.1318355111> [retrieved Feb. 10, 2021], 6 pages.

Khokhlova, T., "In vivo tissue emulsification using millisecond boiling induced by high intensity focused ultrasound," The Journal of the Acoustical Society of America, Apr. 2011 <https://doi.org/10.1121/1.3588149> [retrieved Apr. 21, 2021], 2 pages. (Meeting abstract only—no PDF available).

Maxwell, A., "Boiling histotripsy: A noninvasive method for mechanical tissue disintegration," The Journal of the Acoustical Society of America, Oct. 2014 <https://doi.org/10.1121/1.4900116> [retrieved Jul. 21, 2021], 2 pages. (Meeting abstract only—no PDF available).

Maxwell, A., "Disintegration of tissue using high intensity focused ultrasound: two approaches that utilize shock waves," Acoustics Today, Oct. 2012 <https://acousticstoday.org/wp-content/uploads/2019/09/DISINTEGRATION-OF-TISSUE-USING-HIGH-INTENSITY-FOCUSED-ULTRASOUND-TWO-APPROACHES-THAT-UTILIZE-SHOCK-WAVES-Adam-Maxwell.pdf> [retrieved Feb. 10, 2021], 14 pages.

Maxwell, A., "A Prototype Therapy System for Transcutaneous Application of Boiling Histotripsy," IEEE Xplore, Oct. 2017 <https://https://ieeexplore.ieee.org/document/8010307> [retrieved Sep. 18, 2020], 16 pages.

Pahk K., "Bubble dynamics in boiling histotripsy," Elsevier, Jul. 2018 <https://https://doi.org/10.1016/j.ultrasmedbio.2018.07.025> [retrieved Feb. 10, 2021], 24 pages.

Rosenschein, U., "Ultrasound Imaging-Guided Noninvasive Ultrasound Thrombolysis," AHA Journals, Jul. 2000 <https://www.ahajournals.org/doi/full/10.1161/01.CIR.102.2.238> [retrieved Jul. 23, 2020], 8 pages.

Wang, Y., "Histological and biochemical analysis of mechanical and thermal bioeffects in boiling histotripsy lesions induced by high intensity focused ultrasound," National Institutes of Health, Mar. 2013 <https://pubmed.ncbi.nlm.nih.gov/23312958/> [retrieved Jul. 23, 2020], 28 pages.

(56) References Cited

OTHER PUBLICATIONS

Khokhlova, et al., "Controlled Tissue Emulsification Produced by High Intensity Focused Ultrasound Shock Waves and Millisecond Boiling, " The Journal of the Acoustical Society of America, Nov. 2011, vol. 130, No. 5, Pt. 2, 13 pages.

Cranston, et al., "A Review of High-Intensity Focused Ultrasound in Urology," Cancers 2021, 13, 5696. <https://doi.org/10.3390/cancers13225696>, 9 pages.

D. Cathignol, "High Intensity Piezoelectric Sources for Medical Applications: Technical Aspects," Nonlinear Acoustics at the Beginning of the 21st Century,vol. 1, 8 pages.

Chapelon, et al. "New Piezoelectrics Transducers for Therapeutic Ultrasound," Ultrasound in Medicine and Biology, vol. 26, No. 1, pp. 153-159, 2000, 7 pages.

\* cited by examiner

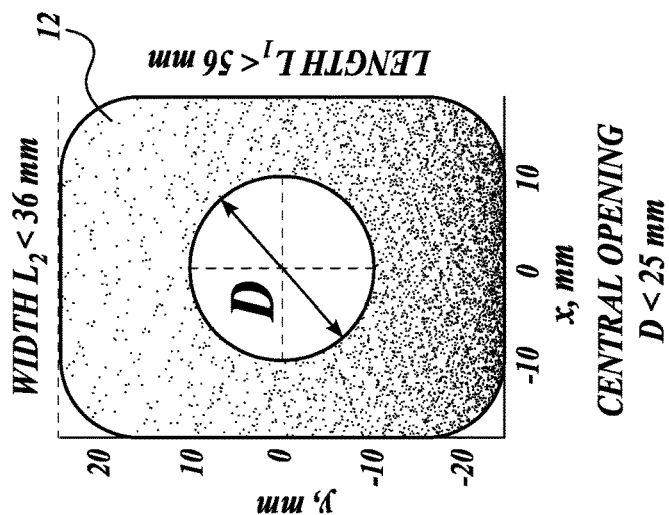
FIG. 4D
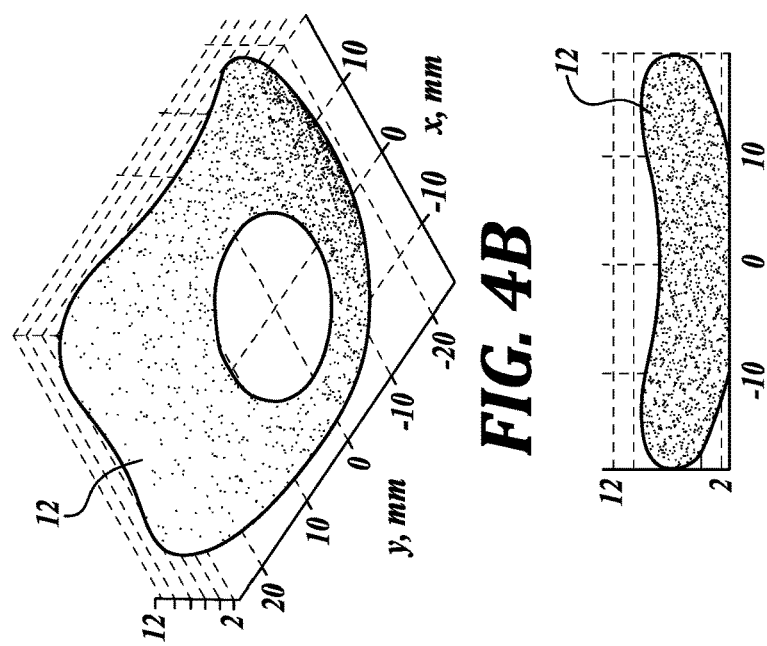
FIG. 4B
FIG. 4C
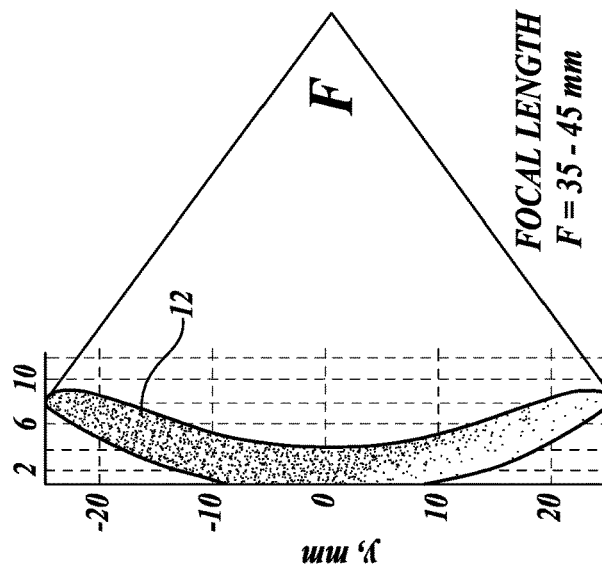
FIG. 4A

FIG. 6A *(PRIOR ART)*

TRANSRECTAL ULTRASOUND PROBE FOR BOILING HISTOTRIPSY ABLATION OF PROSTATE, AND ASSOCIATED SYSTEMS AND METHODS

CROSS-REFERENCE TO RELATED APPLICATION

This application claims the benefit of U.S. Provisional Application No. 62/846,267, filed May 10, 2019, the disclosure of which is expressly incorporated herein by reference in its entirety.

STATEMENT OF GOVERNMENT LICENSE RIGHTS

This invention was made with government support under R21 CA219793, R01 EB023910, R01 GM122859, and R01 EB007643, awarded by the National Institutes of Health. The government has certain rights to the invention.

BACKGROUND

Thermal ablation of prostate tissue with high intensity focused ultrasound (HIFU) has recently received FDA approval as a non-invasive treatment alternative to first-line prostate cancer treatment options. However, conventional clinical transrectal HIFU systems have certain limitations. In particular, conventional transrectal HIFU systems may cause collateral damage due to nearfield heating and heat diffusion from the focus. For example, conventional HIFU treatment of a region of prostate generates heat inside the tissue, which then diffuses into other regions of the prostate and the surrounding tissue, potentially causing thermal damage to otherwise healthy tissue. The conventional systems also suffer from insufficient real-time ability to monitor treatment efficacy. Accordingly, systems and methods are needed for improved ablation and imaging of the prostate or other target tissue.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Briefly, the inventive technology uses boiling histotripsy (BH) to cause precise mechanical tissue ablation, thus destroying a target tissue (e.g., cancer tissue). In operation, a sequence of nonlinear ms-long pulses, each having multiple relatively high amplitude shock fronts, heat target tissue up to boiling temperatures within a μm-scale volume during each pulse and causes localized evaporation bubbles at the focus. Thus-generated evaporation bubbles relatively rapidly grow into a mm-scale vapor bubble and cool down. The interaction between the remaining ultrasound shocks of the pulse and the ensuing vapor bubble results in a precise mechanical tissue ablation.

Furthermore, the bubbles generated by BH and the resulting hyperechogenicity of the sonicated tissue allow for reliable real-time targeting and monitoring the treatment with B-mode ultrasound. Moreover, the loss of structure of mechanically ablated tissue results in hypoechogenicity of the treated volume in B-mode images and allows for evaluation of the treatment outcomes. Owing to the rapidity of tissue ablation bioeffects (e.g., on milliseconds scale), low repetition rate of the pulses, and the mechanical mode of action, BH minimizes nearfield heating, heat-sink effects and thermal spread which otherwise complicate conventional HIFU treatments.

In some embodiments, a shaped ultrasound therapy transducer for BH is about 50 mm long and about 35 mm wide, therefore being suitable for a transrectal use. In different embodiments, the therapy transducer may have a focal length of about 40 mm and an aperture of 35×50 mm. The ultrasound therapy transducer may include a central opening for an ultrasound imaging transducer. In some embodiments, the opening is circular having a diameter in a range of 20 mm to 25 mm.

In some embodiments, the therapy ultrasound waves are generated as bursts of waves that are separated by non-emitting periods of time. In some embodiments, the BH pulses have 5 ms duration, 2 Hz pulse repetition frequency, and 20 pulses/focus. These pulses may be delivered to a rectangular grid (6×6 mm with 2 mm spacing) within target tissue using a 1.5 MHz transducer. The surface intensity of the therapy transducer (defined as the power generated per surface area of the transducer) may range from 10 W/cm2 to 80 W/cm2. Based on this level of the surface intensity, the ultrasound shock waves may reach a shock amplitude of about 100 MPa at a focus depth of 40 mm. Such shock amplitude suffices to initiate BH (e.g., to initiate bubble activity). In some embodiments, the therapy transducer operates in a frequency range of 1 MHz to 2.8 MHz.

In one embodiment, a method for a transrectal ultrasound treatment using high intensity focused ultrasound (HIFU) includes: generating a boiling histotripsy (BH) therapy ultrasound by a therapy transducer in a frequency range of 1 MHz to 2.8 MHz and a surface intensity range of 10 W/cm2 to 80 W/cm2, where the therapy transducer is about 50 mm long and about 35 mm wide; applying the therapy ultrasound by directing ultrasound pulses having ultrasound shock waves to a target tissue at a focal depth of 2.5 cm to 5.5 cm; generating at least one μm-scale vapor bubble at a target region; growing the at least one vapor bubble to at least one mm-scale bubble; and mechanically disintegrating a surrounding tissue by interactions between the at least one mm-scale bubble and the ultrasound shock waves within a pulse.

In an embodiment, a focal region for the therapy ultrasound at the target tissue is 0.1 mm to 1 mm wide and 2 mm to 10 mm long.

In another embodiment, a shock amplitude of the therapy ultrasound at a focus depth of 40 mm is about 100 MPa. In an embodiment, a power of the therapy ultrasound is about 200 Watt at the focus depth of 40 mm.

In one embodiment, the therapy transducer is a phased array therapy transducer comprising a plurality of phased array elements.

In an embodiment, the phased array elements are ring-like structures of an annular array. In another embodiment, a phased array therapy transducer comprises 8 phased array elements. In an embodiment, the phased array elements are tile-like structures of a mosaic array.

In one embodiment, the method also includes generating an imaging ultrasound in a frequency range of 7 MHz to 15 MHz by an imaging transducer. In an embodiment, the imaging transducer is placed within a circular hole in the therapy transducer, and wherein a diameter of the hole in the therapy transducer is in a range of 20 mm to 25 mm. In another embodiment, the imaging transducer is configured within a rectangular hole in the therapy transducer, and wherein the hole in the therapy transducer is about 13 mm wide and about 16 mm long.

In one embodiment, a transrectal high intensity focused ultrasound (HIFU) device, includes: a boiling histotripsy (BH) ultrasound probe having a generally rectangular therapy transducer configured to emit therapy ultrasound in an ultrasound frequency range of 1 MHz to 2.8 MHz at a surface acoustic intensity of in a range of 10 W/cm2 to 80 W/cm2, the therapy transducer being about 50 mm long and about 35 mm wide and having a centrally located opening, wherein the therapy transducer is configured to generate shock waves at a focal depth of 2.5 cm to 5.5 cm.

In an embodiment, a focal region of the therapy ultrasound at the target tissue is 0.1 mm to 2 mm wide and 2 mm to 10 mm long.

In another embodiment, the shock waves have an amplitude of the therapy ultrasound of about 100 MPa at a focus depth of 40 mm.

In one embodiment, a power of the therapy ultrasound is about 200 Watt at the focus depth of 40 mm.

In one embodiment, the device also includes: generating an imaging ultrasound in a frequency range of 7 MHz to 15 MHz by an imaging transducer.

In one embodiment, the device also includes an imaging transducer configured to generate an imaging ultrasound in a frequency range of 7 MHz to 15 MHz, where the imaging transducer is configured within a central opening in the therapy transducer, and where the dimensions of the opening are in a range of 15 mm to 25 mm.

In one embodiment, an imaging transducer is configured to generate an imaging ultrasound in a frequency range of 7 MHz to 15 MHz, where the imaging transducer is configured within a rectangular hole in the therapy transducer, and where the hole is about 13 mm wide and about 16 mm long.

In one embodiment, the therapy transducer is a phased array therapy transducer comprising a plurality of phased array elements, and the phased array elements are ring-like structures of an annular array.

In one embodiment, the therapy transducer is a phased array therapy transducer comprising a plurality of phased array elements, and the phased array elements are tile-like structures of a mosaic array.

DESCRIPTION OF THE DRAWINGS

The foregoing aspects and many of the attendant advantages of this inventive technology will become more readily appreciated as the same become better understood by reference to the following detailed description, when taken in conjunction with the accompanying drawings, wherein:

FIGS. 4A-4D are different views of a HIFU transrectal therapy transducer in accordance with an embodiment of the present technology;

FIGS. 6A and 6B illustrate ultrasound wave propagation according to prior art and present technology, respectively;

DETAILED DESCRIPTION

Example devices, methods, and systems are described herein. It should be understood the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood aspects of the present disclosure, as generally described herein, and illustrated in the figures, can be arranged, substituted, combined, separated, and designed in a wide variety of different configurations, all of which are explicitly contemplated herein.

Figure 1:
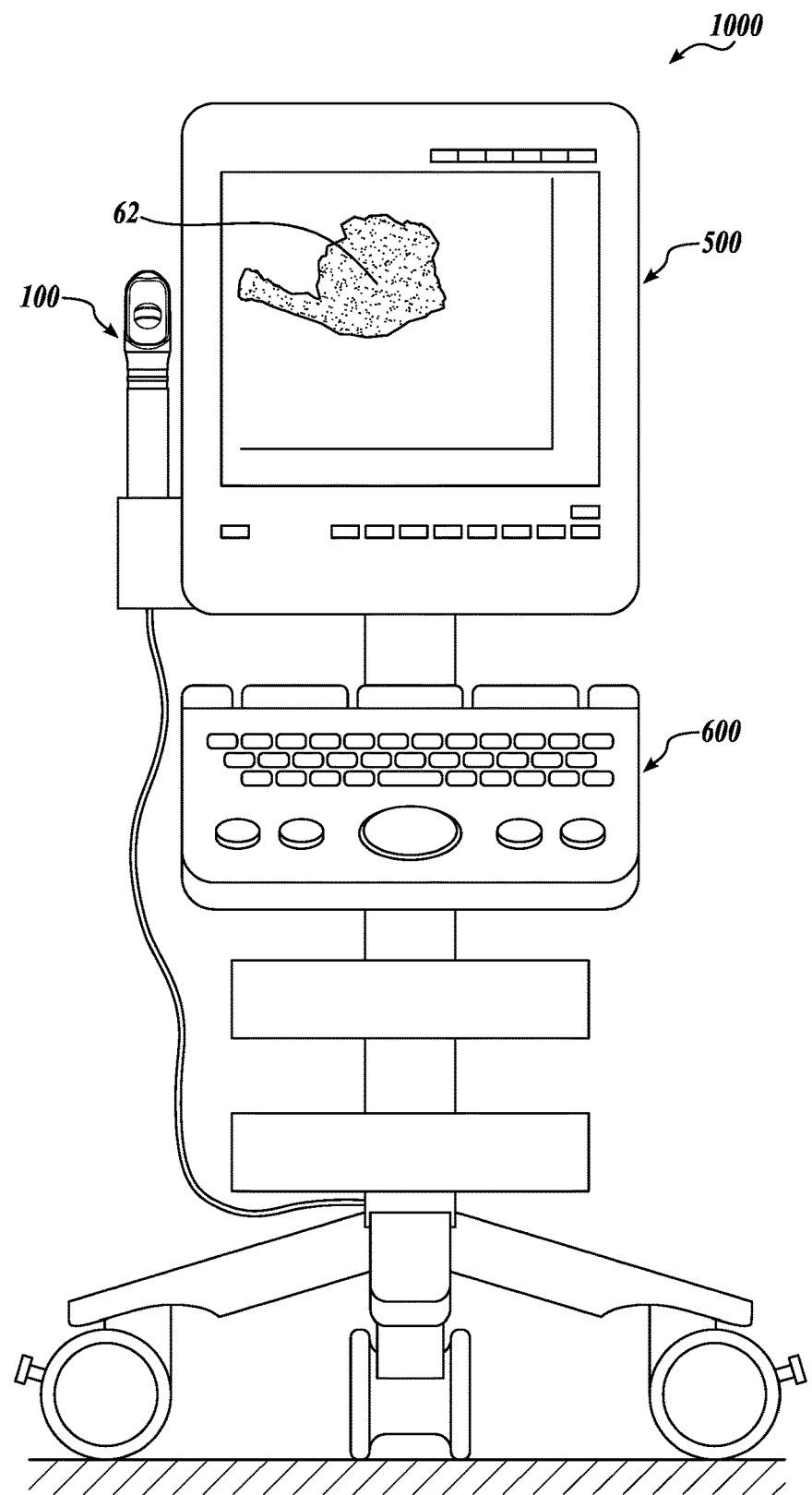
FIG. 1 is a schematic diagram of a system for transrectal ultrasound boiling histotripsy ablation in accordance with an embodiment of the present technology.

FIG. 1 is a schematic diagram of a system for transrectal ultrasound boiling histotripsy ablation in accordance with an embodiment of the present technology. An ultrasound system 1000 includes an ultrasound probe 100 having a therapy transducer and optionally an imaging transducer. The ultrasound probe 100 may be controlled by a controller (e.g., a computer) 600 having suitable software and commands for controlling the ultrasound. A monitor 500 can display images 62 of the target tissue that are obtained, for example, by an imaging transducer of the ultrasound probe 100 or by a separate imaging device.

Figure 2:
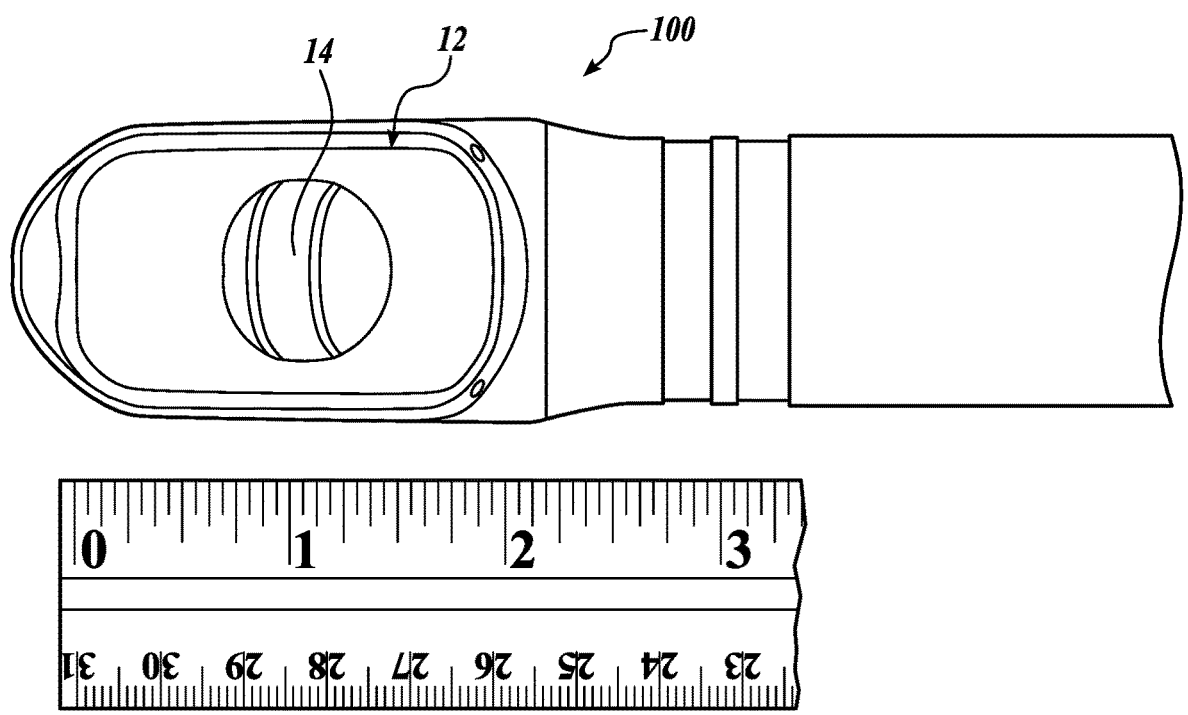
FIG. 2 is a front view of an ultrasound probe in accordance with an embodiment of the present technology.

FIG. 2 is a front view of an ultrasound probe 100 in accordance with an embodiment of the present technology. The illustrated ultrasound probe includes a therapy transducer 12 and an imaging transducer 14 that is located in an opening of the therapy transducer. In different embodiments, the imaging transducer may be located away from the therapy transducer 12. In some embodiments, the dimensions of the probe 100 are suitable for transrectal use when treating patient's prostate. For example, the imaging transducer 14 may be about 25 mm long and about 8 mm wide. In some embodiments, the imaging transducer 14 generates imaging ultrasound at a frequency range of 7-15 MHz.

Figure 3:
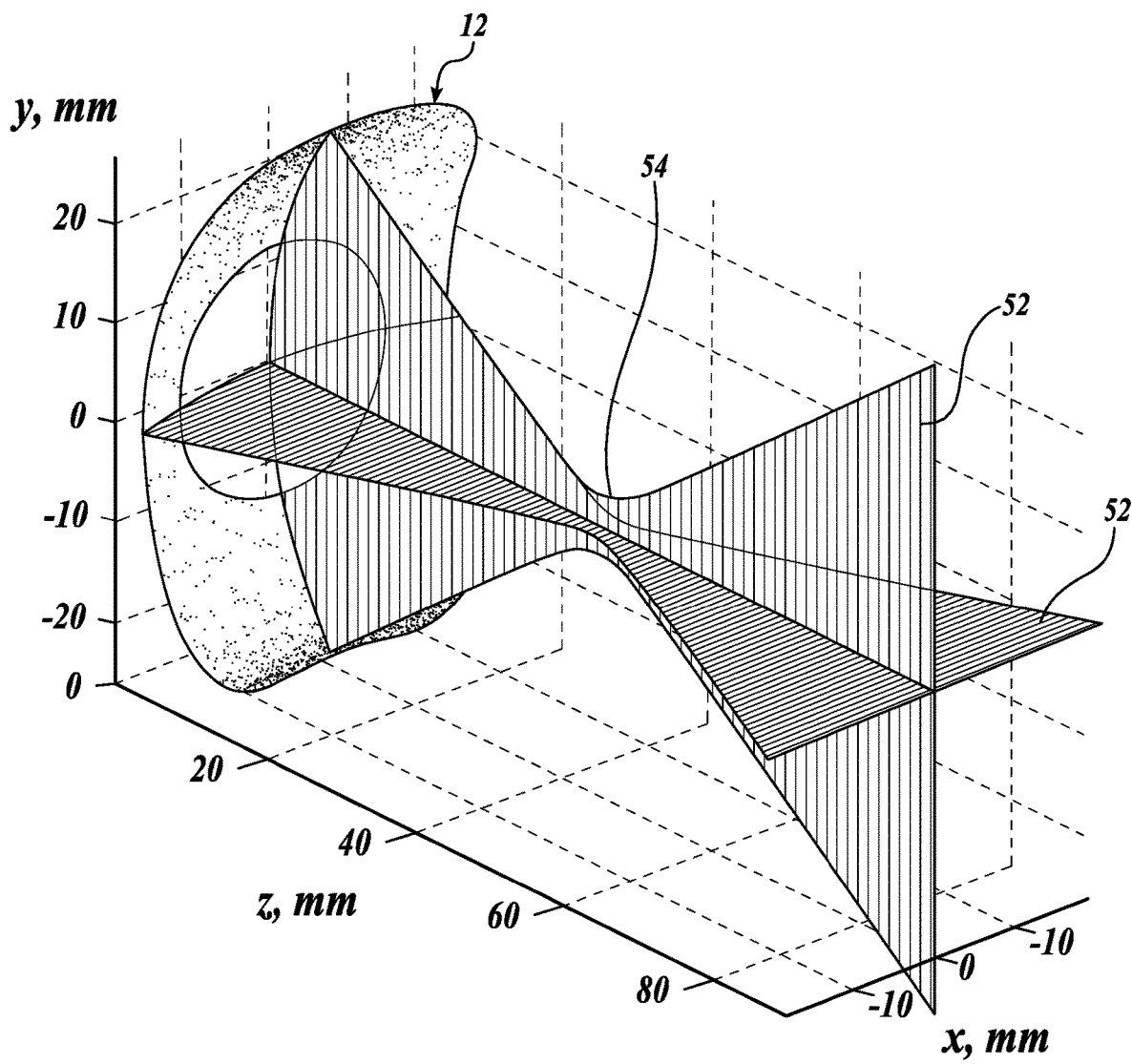
FIG. 3 is a diagram of an ultrasound field generated by a HIFU transrectal transducer for treating prostate tissue in accordance with an embodiment of the present technology.

FIG. 3 is a diagram of an ultrasound field generated by a HIFU transrectal transducer for treating prostate tissue in accordance with an embodiment of the present technology. The therapy transducer 12 is located in the X-Y plane of the illustrated 3D coordinated system. The central opening of the therapy transducer 12 may be suitable for holding an imaging transducer. As illustrated in the graph, a sample therapy transducer 12 is about 50 mm long and about 35 mm wide. However, in different embodiments the therapy transducer may have different dimensions.

In operation, therapy transducer 12 generates an ultrasound field 52. In some embodiments, a focal region 54 of the ultrasound field 52 is about 40 mm away from the therapy transducer. The focal area is about 5 mm long and 1 mm wide at low power and linear focusing conditions. For boiling histotripsy conditions, the focal area for the shock amplitude of the pulse is about 2.5 mm by 0.1 mm.

FIGS. 4A-4D are different views of a HIFU transrectal therapy transducer in accordance with an embodiment of the present technology. Illustrated therapy transducer 12 may operate at a frequency range of 1-3 MHz, 1.5-2.8 MHz, 1-2.8 MHz, 2-2.8 MHz, or similar. In some embodiments, the therapy transducer 12 generates ultrasound shocks of about 60-140 MPa in a target tissue located at a focal region about 35-55 mm away from the transducer. In different embodiments, a surface intensity of the therapy transducer (defined as the power generated per unit surface area of the transducer) may range from 10 W/cm2 to 80 W/cm2 or from 10 W/cm2 to 40 W/cm2. In some embodiments, the therapy transducer includes a central opening having a diameter of up to 25 mm. Such central opening may be suitable for an imaging transducer.

FIGS. 5A-5D are different views of phased array HIFU transrectal therapy transducers in accordance with embodiments of the present technology. In each case, the therapy transducer 12 has a generally rectangular shape with 50 mm length ($L_1$) and 35 mm width ($L_2$). A radius of curvature (i.e., the focal length) of the therapy transducer is 40 mm. In other embodiments, other curvatures are possible. In some embodiments, the therapy transducers may have curved edges with about 10 mm radius.

Figure 5A:
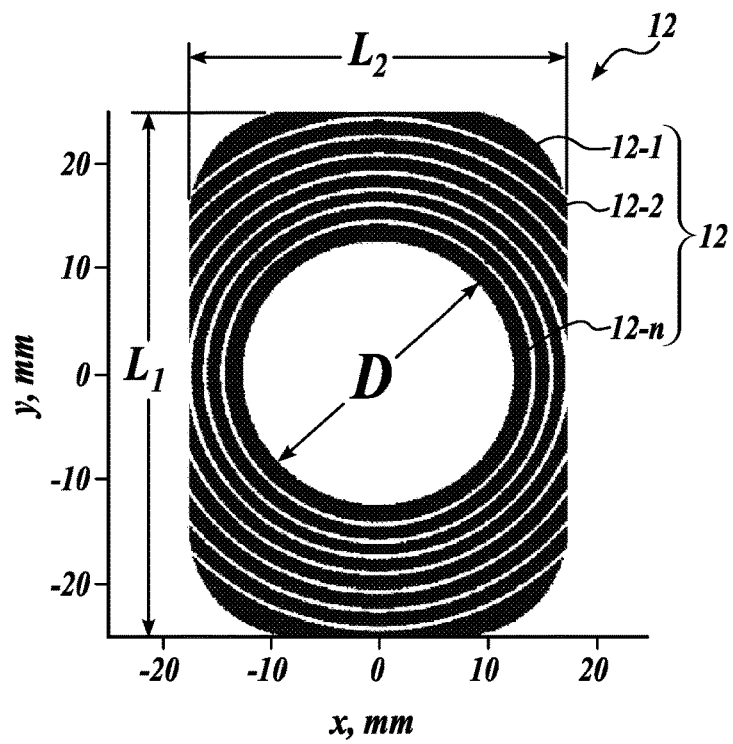
FIGS. 5A-5D are different views of phased array HIFU transrectal therapy transducers in accordance with embodiments of the present technology.

FIG. 5A illustrates a phased array therapy transducer 12 having eight ring-like elements 12-$i$ (also referred to as sections or rings) of equal area. The total area of the illustrated therapy transducer 12 is 1353 mm2. In other embodiments, different number of elements may be used, and the elements may have different areas. For the phased annular array therapy transducer, the focus can be electronically steered along the axis. In some embodiments, the phased array therapy transducer 12 may be controlled to provide a range of steering such that the focal area stays within a region limited by at most 80% decrease of the focal intensity. In different embodiments, other restrictions to steering angle or depth may be implemented. The illustrated therapy transducer has a central opening with a 15-25 mm diameter (D).

Figure 5B:
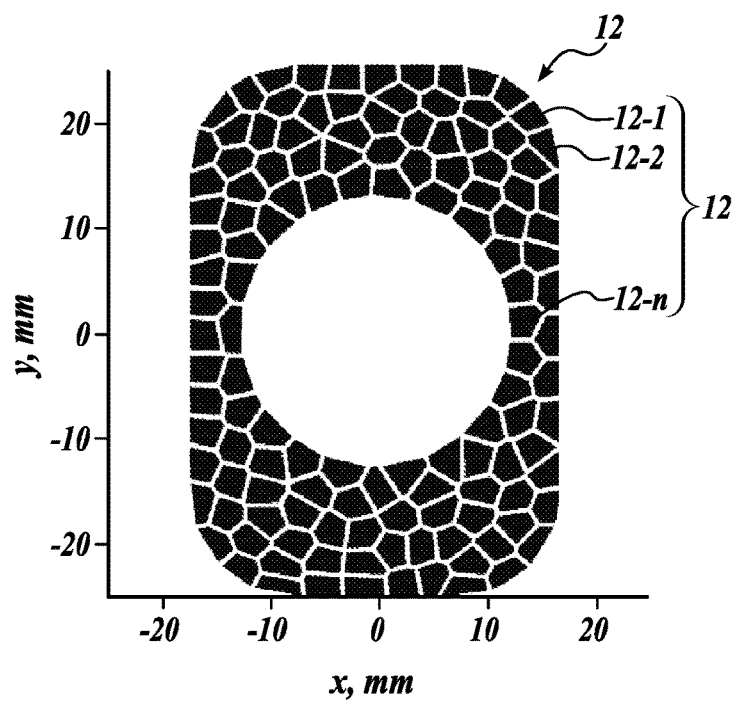

FIG. 5B illustrates a phased array therapy transducer 12 having 128 mosaic- or tile-like elements 12-$i$ of equal area. In operation, elements 12-$i$ may be controlled individually or in predetermined groups.

Figure 5C:
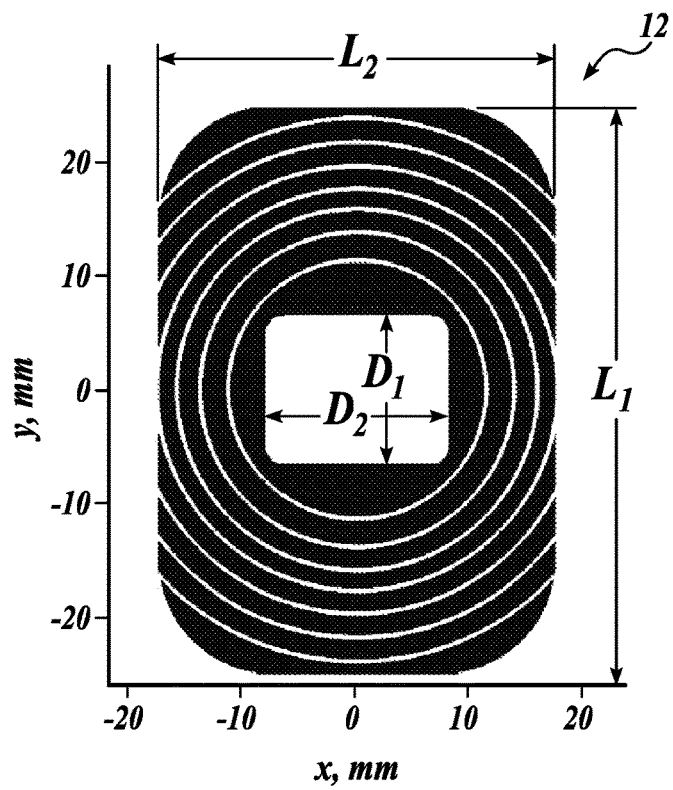
Figure 5D:
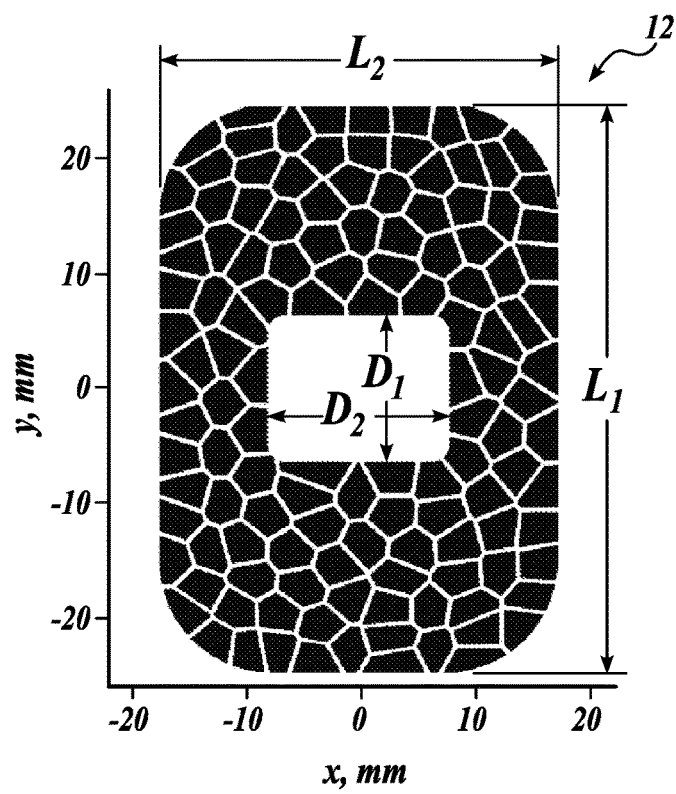

The therapy transducers illustrated in FIGS. 5C and 5D generally correspond to those of FIGS. 5A and 5D except for the rectangular openings for the imaging transducer. In some embodiments, these openings may be 16 mm wide ($D_1$) and 13 mm high ($D_2$), leaving a total area of the therapy transducer at 1648 mm2.

Figure 6B:
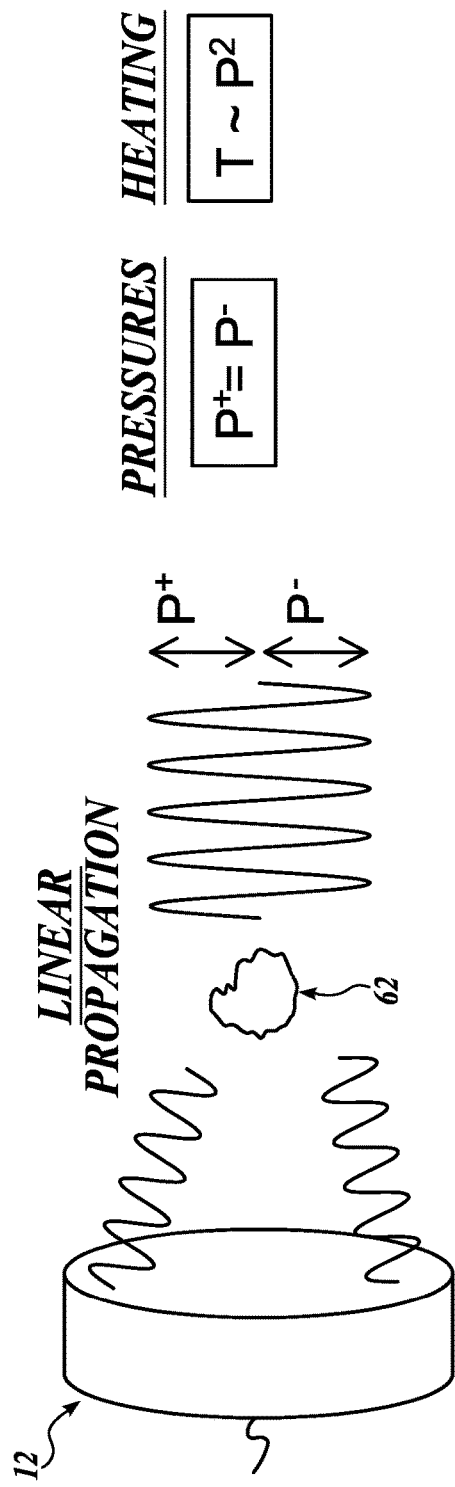
Figure 6B:
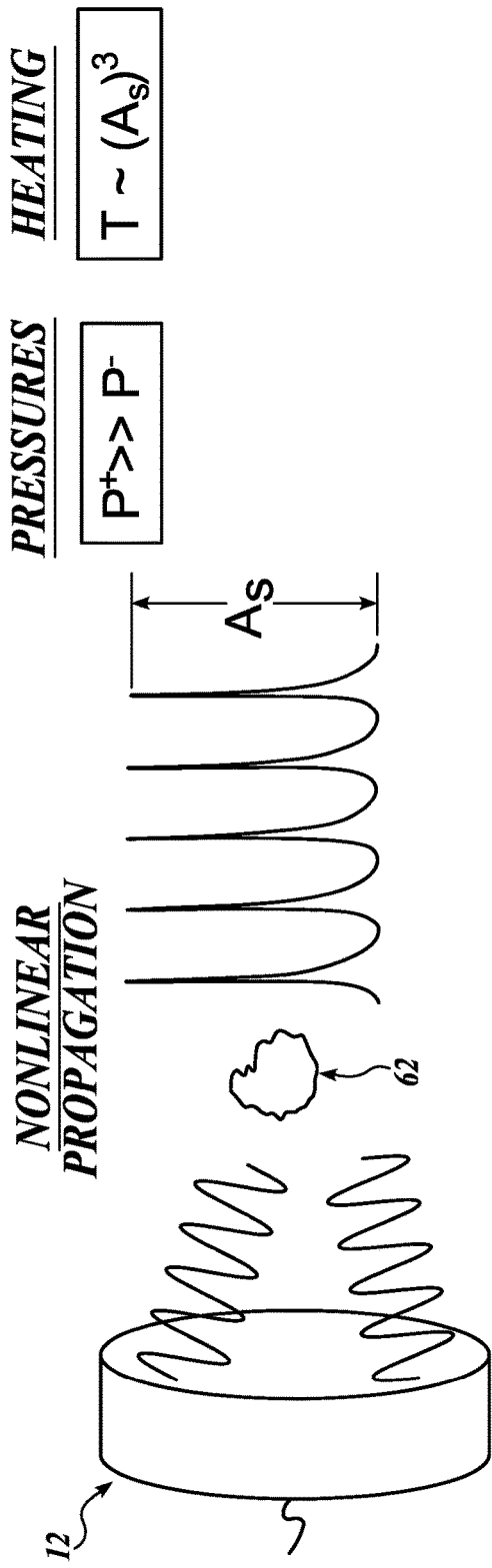

FIGS. 6A and 6B illustrate ultrasound wave propagation according to prior art and present technology, respectively. Both FIGS. 6A and 6B illustrate ultrasound waves generated by therapy transducers 12. The ultrasound waves target tissue 62 (e.g., tumor, blood vessel).

FIG. 6A illustrates the conventional technology that uses smooth waves having generally same peaks of the positive pressure and negative pressure ($P^+$ and $P^-$). The conventional technology has certain shortcomings. For example, the smooth ultrasound waves slowly heat tissue and, when applied over a period of time, the heat diffuses to tissues that surrounds the target tissue at the focus. In many applications, such heating must be minimized or controlled by, for example, by limiting the exposure time or energy of the therapy ultrasound. In general, with conventional smooth wave technology a heat generated by the ultrasound scales with square of pressure peaks of the ultrasound ($P^2$).

FIG. 6B illustrates an embodiment of the inventive technology. With the inventive technology, the emitted smooth therapy ultrasound waves develop into nonlinear shock waves as they propagate through the tissue. These nonlinear shock waves are characterized by their positive pressure ($P^+$) being significantly higher than the negative pressure ($P^-$). Furthermore, ultrasound shock waves heat the target tissue relatively fast, since the heat generation scales with the ultrasound shock wave amplitude to third power ($As^3$). As a result, a boiling temperature may be reached relatively fast, for example within several milliseconds, thus limiting the undesired heating of the surrounding tissue. The vapor bubble initiated by the localized μm scale boiling relatively quickly grows into larger vapor cavity and cools down while expanding from the hot focus. In some embodiments, relatively small vapor bubble having μm-scale may grow into mm-scale bubble within milliseconds. The remaining shock wavefronts within the same pulse keep interacting with these bubbles. As explained above, interaction of upcoming shocks with large scale bubble mechanically destroy (ablate) target tissue.

Figure 7A:
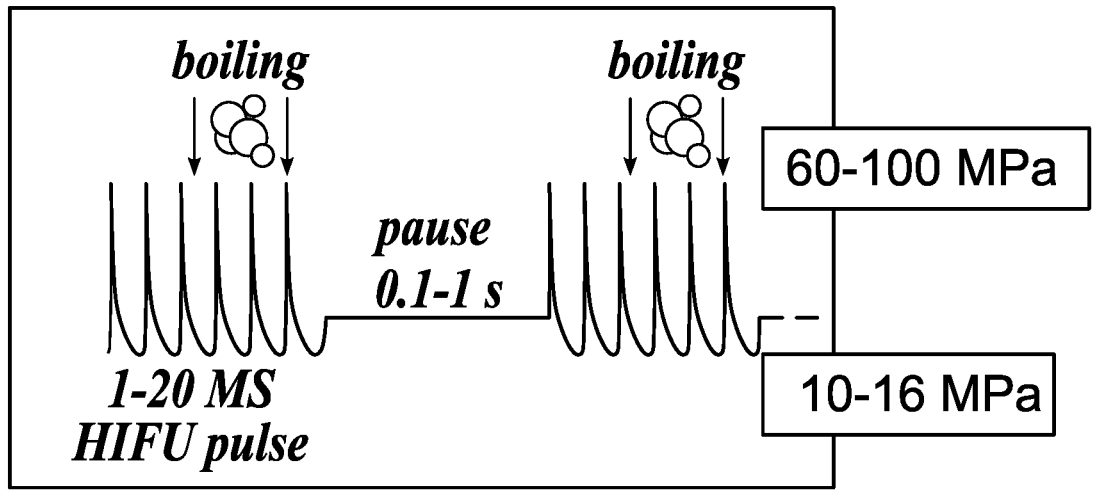
FIG. 7A is a graph of HIFU wave duty cycle in accordance with an embodiment of the present technology.
Figure 7B:
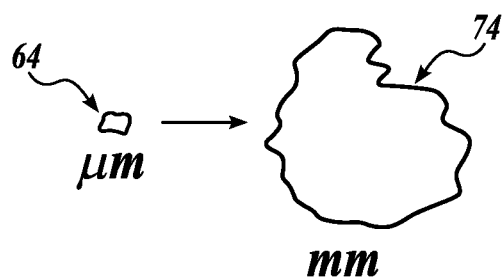
FIG. 7B illustrates growth of HIFU-caused vapor bubbles in accordance with an embodiment of the present technology.

FIG. 7A is a graph of HIFU pressure pulses in accordance with an embodiment of the present technology. In some embodiments, the pulses of HIFU may extends over 1-20 ms, followed by a pause of 0.1-2 second. As explained above, the ultrasound shock waves within a given pulse may cause localized boiling in the target tissue, therefore generating vapor bubbles at the focal area. Next, these vapor bubbles may rapidly grow into significantly larger vapor bubble during the same pulse in the HIFU operation. These bubbles interact with remaining shock wavefronts within the same pulse. An example of such rapid growth in the bubble size is illustrated in FIG. 7B, which shows an initially generated vapor bubble 64 at μm-scale growing into a mm-scale gas bubble 74.

Figure 8:
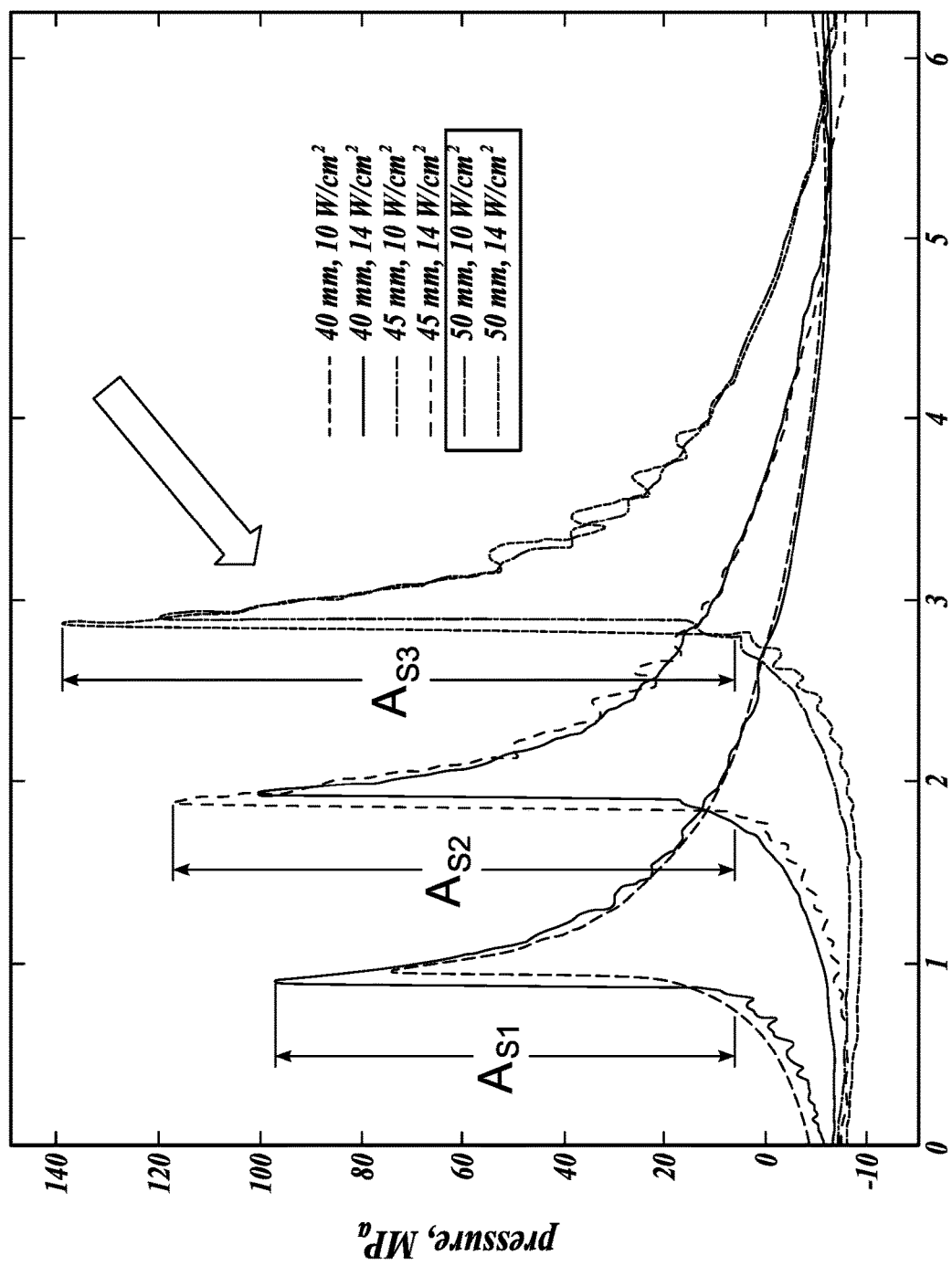
FIG. 8 is a graph of one cycle of HIFU focal waveform in accordance with an embodiment of the present technology.

FIG. 8 is a graph of one cycle of HIFU focal waveforms in accordance with an embodiment of the present technology. The horizontal axis represents time elapsed, and the vertical axis represents pressure at the target area. FIG. 8 shows modeled focal waveforms in tissue produced by the HIFU probe 100. As explained above, the HIFU system 100 can generate ultrasound shock waveforms in the focal region of the therapy transducer. In some embodiments, the pressure amplitudes of shock waveforms (As) may range from about 60 MPa to about 140 MPa. In general, the pressure amplitudes of the shock waveforms scale up with higher surface intensity and longer length of the therapy transducer. For example, for a focal length of 40 mm, probe length of 40 mm and surface intensity of 14 W/cm2, the pressure amplitude $A_{s1}$ is about 95 MPa. For a higher value of the probe length of 50 mm and the same surface intensity of 14 W/m2, the pressure amplitude $A_{s3}$ is about 140 MPa, at least in part because for transducers with larger focusing angle, the focal lobe is shorter, the ultrasound shock waves have a shorter distance to develop thus requiring higher pressures. Other values of illustrated parameters are also possible in different embodiments.

Figure 9A:
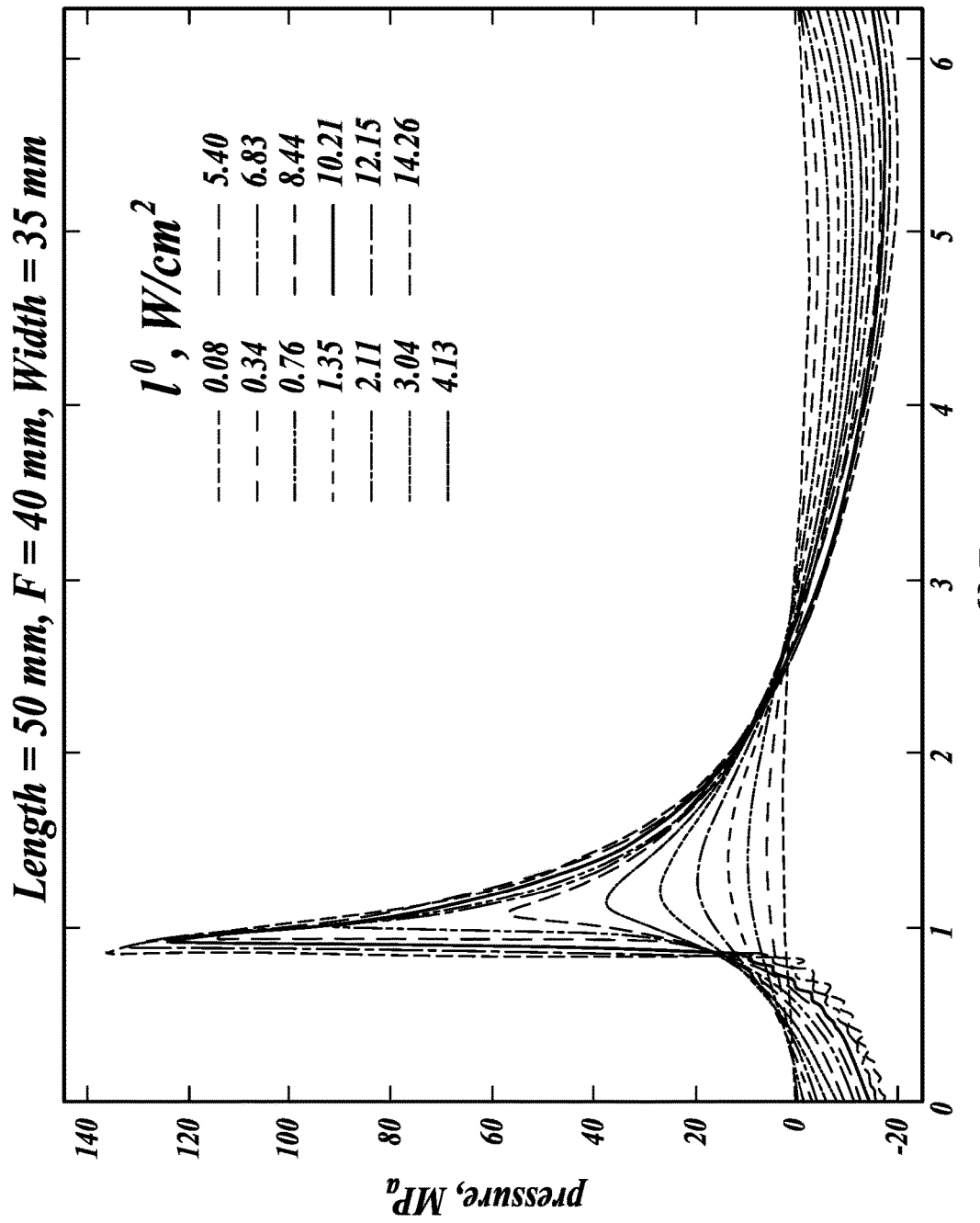
FIGS. 9A and 9B are graphs of one cycle of HIFU focal waveform in accordance with an embodiment of the present technology.

FIG. 9A is a graph of one cycle of HIFU focal waveforms in accordance with an embodiment of the present technology. The horizontal axis represents time elapsed, and the vertical axis represents pressure at the target area. The graph shows modeled pressure results in water for a therapy probe having 50 mm length and 35 mm width, at the focal length of 40 mm. Different curves in the graph represent surface intensity of the modeled probe in a range of 0.08 W/cm2 to 14.26 W/cm2. The resultant ultrasound pressures at the focus scale up with the increased surface intensity. Furthermore, for the modeled probe, the shock waves develop only after a certain threshold value of the surface intensity is reached, which in this case is about 10 W/cm2. In other embodiments, other values of the parameters may apply.

Figure 9B:
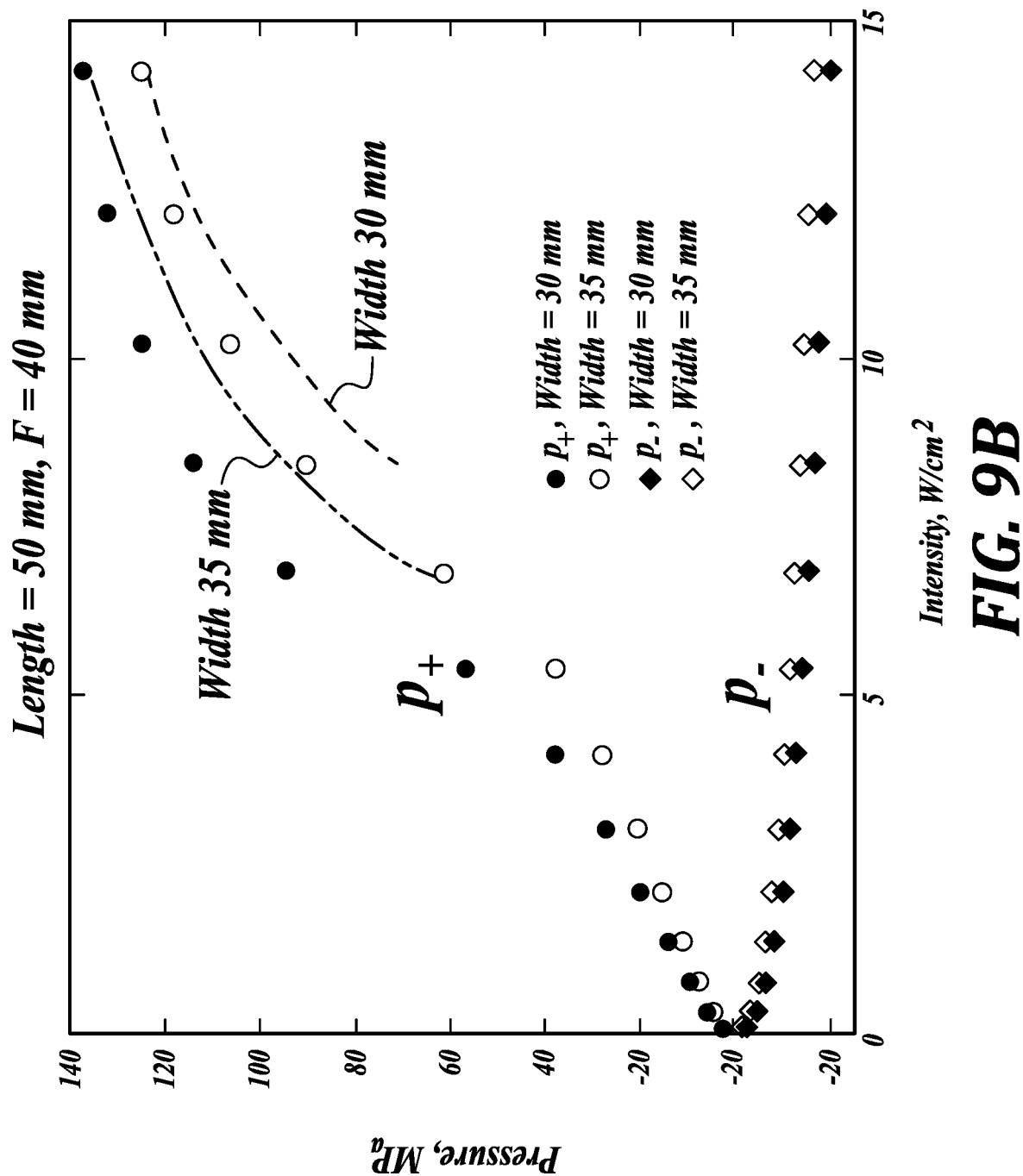

FIG. 9B is a graph of HIFU peak positive and peak negative pressures of the focal waveform in accordance with an embodiment of the present technology. The horizontal axis represents surface intensity of the therapy probe, and the vertical axis represents peak pressures at the target area. The graph shows modeled pressure results for a therapy probe having 50 mm length and the focal length of 40 mm. Two therapy probes are modeled: one having a width of 30 mm (solid symbols) and another having a width of 35 mm (open symbols). Based on the simulation results, the positive peak pressure ($P^+$) and the resultant ultrasound shock amplitude increases with increased probe width.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. For example, in some embodiments the counter or controller may be based on a low-power buck regulator connected to a capacitor. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

The present application may also reference quantities and numbers. Unless specifically stated, such quantities and numbers are not to be considered restrictive, but exemplary of the possible quantities or numbers associated with the present application. Also, in this regard, the present application may use the term "plurality" to reference a quantity or number. In this regard, the term "plurality" is meant to be any number that is more than one, for example, two, three, four, five, etc. The terms "about," "approximately," etc., mean plus or minus 5% of the stated value.

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

What is claimed is:

1. A method for a transrectal ultrasound treatment using high intensity focused ultrasound (HIFU), the method comprising:
generating boiling histotripsy (BH) therapy ultrasound by a therapy transducer operating in a frequency range of 1 MHz to 2.8 MHz and having a surface intensity of the therapy transducer in a range of 10 W/cm2 to 80 W/cm2, wherein the therapy transducer is about 50 mm long and about 35 mm wide;
applying the therapy ultrasound by directing a plurality of ultrasound pulses having ultrasound shock waves to a target tissue at a focal depth of 2.5 cm to 5.5 cm;
generating at least one μm-scale vapor bubble at the target tissue;
growing the at least one vapor bubble to at least one mm-scale bubble; and
mechanically disintegrating the target tissue by interactions between the at least one mm-scale bubble and the ultrasound shock waves, wherein the interactions take place within a duration of individual ultrasound pulses of the plurality of ultrasound pulses, without thermally damaging a surrounding tissue.

2. The method of claim 1, wherein a focal region for the therapy ultrasound at the target tissue is 0.1 mm to 1 mm wide and 2 mm to 10 mm long.

3. The method of claim 1, wherein a shock amplitude of the therapy ultrasound at a focus depth of 40 mm is about 100 MPa.

4. The method of claim 3, wherein a power of the therapy ultrasound is about 200 Watts at the focus depth of 40 mm.

5. The method of claim 1, wherein the therapy transducer is a phased array therapy transducer comprising a plurality of phased array elements.

6. The method of claim 5, wherein the phased array elements are ring structures of an annular array.

7. The method of claim 6, wherein the phased array therapy transducer comprises 8 phased array elements.

8. The method of claim 5, wherein the phased array elements are tile structures of a mosaic array.

9. The method of claim 1, further comprising:
generating imaging ultrasound in a frequency range of 7 MHz to 15 MHz by an imaging transducer.

10. The method of claim 9, wherein the imaging transducer is placed within a circular hole in the therapy transducer, and wherein a diameter of the hole in the therapy transducer is in a range of 20 mm to 25 mm.

11. The method of claim 9, wherein the imaging transducer is configured within a rectangular hole in the therapy transducer, and wherein the hole in the therapy transducer is about 13 mm wide and about 16 mm long.

12. A transrectal high intensity focused ultrasound (HIFU) device, comprising:
a boiling histotripsy (BH) ultrasound probe having a generally rectangular therapy transducer configured to emit therapy ultrasound in an ultrasound frequency range of 1 MHz to 2.8 MHz at a surface acoustic intensity of the ultrasound probe in a range of 10 W/cm2 to 80 W/cm2, the therapy transducer being about 50 mm long and about 35 mm wide and having a centrally located opening, wherein the therapy transducer is configured to generate shock waves at a focal depth of 2.5 cm to 5.5 cm, and wherein the therapy transducer is configured for mechanically disintegrating a target tissue by interactions between at least one mm-scale bubble and the shock waves, wherein the interactions take place within a duration of a pulse, without thermally damaging a surrounding tissue.

13. The device of claim 12, wherein a focal region of the therapy ultrasound at the target tissue is 0.1 mm to 2 mm wide and 2 mm to 10 mm long.

14. The device of claim 12, wherein the shock waves have an amplitude of the therapy ultrasound of about 100 MPa at a focus depth of 40 mm.

15. The device of claim 12, wherein a power of the therapy ultrasound is about 200 Watts at a focus depth of 40 mm.

16. The device of claim 12, further comprising:
an imaging transducer configured for generating an imaging ultrasound in a frequency range of 7 MHz to 15 MHz.

17. The device of claim 12, further comprising an imaging transducer configured to generate imaging ultrasound in a frequency range of 7 MHz to 15 MHz, wherein the imaging transducer is configured within a central opening in the therapy transducer, and wherein a diameter of the hole in the therapy transducer is in a range of 20 mm to 25 mm.

18. The device of claim 12, further comprising an imaging transducer configured to generate imaging ultrasound in a frequency range of 7 MHz to 15 MHz, wherein the imaging transducer is configured within a rectangular hole in the therapy transducer, and wherein the hole is about 13 mm wide and about 16 mm long.

19. The device of claim 12, wherein the therapy transducer is a phased array therapy transducer comprising a plurality of phased array elements, and wherein the phased array elements are ring structures of an annular array.

20. The device of claim 12, wherein the therapy transducer is a phased array therapy transducer comprising a plurality of phased array elements, and wherein the phased array elements are tile structures of a mosaic array.

* * * * *